Figure 1A:
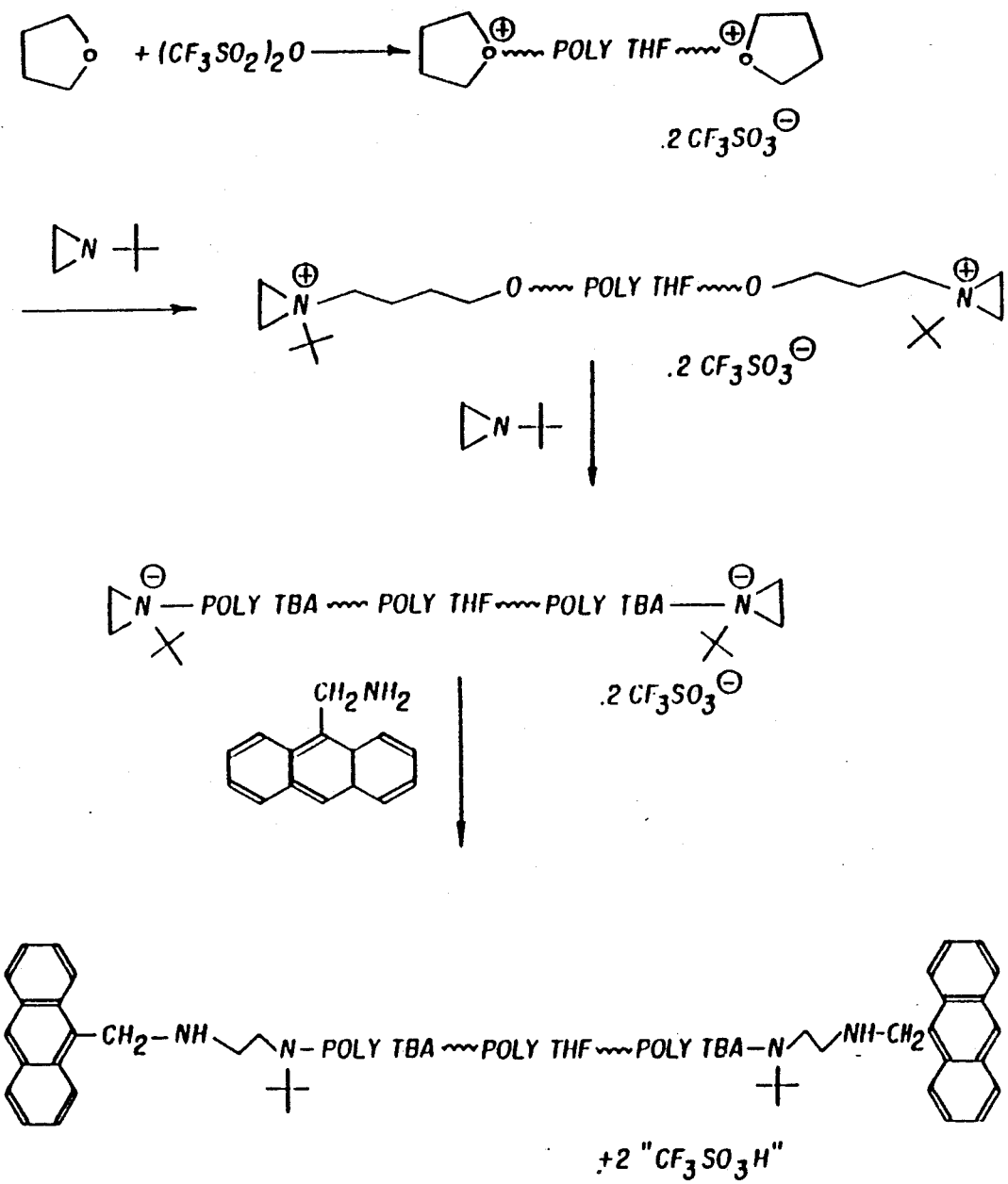

United States Patent [19]

Goethals et al.

[11] Patent Number: 5,035,783

[45] Date of Patent: Jul. 30, 1991

[54] METHOD FOR THE PHOTOCHEMICAL CONVERSION OF TACHYSTEROL COMPOUNDS INTO PREVITAMIN D COMPOUNDS AND OF TRANS-VITAMIN D COMPOUNDS INTO CIS-VITAMIN D COMPOUNDS

[75] Inventors: Eric Goethals, Gent, Belgium; Sebastianus J. Halkes; Robert B. Koolstra, both of Weesp, Netherlands

[73] Assignee: Duphar International Research B.V., Weesp, Netherlands

[21] Appl. No.: 447,509

[22] Filed: Dec. 7, 1989

[30] Foreign Application Priority Data

Dec. 12, 1988 [NL] Netherlands .................. 8803040

[51] Int. Cl.$^5$ ............................................. B01J 19/08
[52] U.S. Cl. ............................................. 204/157.67
[58] Field of Search ...................... 204/157.67, 157.6

[56] References Cited

U.S. PATENT DOCUMENTS

| | | | |
|---|---|---|---|
| 4,517,125 | 5/1985 | Takayama | 204/157.67 |
| 4,551,214 | 11/1985 | Hansen | 204/157.67 |
| 4,609,444 | 9/1986 | Guillet | 204/157.6 |
| 4,686,023 | 8/1987 | Stevens | 204/157.67 |
| 4,849,076 | 7/1989 | Neckeys | 204/157.6 X |

Primary Examiner—John F. Niebling
Assistant Examiner—Ben C. Hsing
Attorney, Agent, or Firm—Stevens, Davis, Miller & Mosher

[57] ABSTRACT

The invention relates to a method for the photochemical conversion of tachysterol compounds into previtamin D compounds and of trans-vitamin D compounds into cis-vitamin D compounds under the influence of radiation, by exposing the tachysterol compound and trans-vitamin D compound, respectively, dissolved in a suitable solvent system, in the presence of a polymeric photosensitizer consisting of a polymer chain ("backbone") comprising covalently bound sensitizers suitable for the photochemical conversion, to light with a wavelength of preferably between approx. 300 and approx. 1,000 nm, and by then isolating the resulting previtamin D compound and cis-vitamin D compound, respectively, in which a polymeric photosensitizer is used, the polymer chain of which has been selected from the group consisting of a polyether chain, an amino groups-containing polymer chain and a block copolymer chain comprising polyether segments and/or amino groups-containing polymer segments, in such a manner that the polymeric photosensitizer dissolves in the solvent system during the exposure to radiation but either upon cooling precipitates from the solution and can be separated, or, in case said polymer chain comprises amino groups, can be protonated with a suitable acid substance and be removed in an after-treatment. The invention also relates to a polymeric photosensitizer to be used for the said method.

9 Claims, 2 Drawing Sheets

METHOD FOR THE PHOTOCHEMICAL CONVERSION OF TACHYSTEROL COMPOUNDS INTO PREVITAMIN D COMPOUNDS AND OF TRANS-VITAMIN D COMPOUNDS INTO CIS-VITAMIN D COMPOUNDS

The invention relates to a method for the photochemical conversion of tachysterol compounds into previtamin D compounds by means of irradiation with light of approx. 300 to approx 1,000 nm. The invention also includes the photochemical conversion of trans-vitamin D compounds into the corresponding cis-vitamin D compounds.

According to U.S. Pat. No. 4,686,023. tachysterol$_2$ or tachysterol$_3$ can be converted photochemically in a high yield into previtamin D$_2$ or previtamin D$_3$ by carrying out the irradiation in the presence of anthracene as a photosensitizer. The resulting previtamin D compounds easily isomerise under the influence of heat to vitamin D compounds, for example, vitamin D$_2$ and vitamin D$_3$. It is known that other sensitizers can also stimulate the above photochemical conversion.

However, the use of photosensitizers in the production of vitamin D compounds has for its disadvantage that it is difficult to remove the used photosensitizer from the final product. In connection with the intended use, namely for humane or veterinary administration, the vitamin D compound, however, should be produced free from detrimental by-products. This means that after the photochemical conversion it should be possible to remove the photosensitizer easily and completely from the resulting vitamin D product.

Slemon (European Patent Application 252740) has recognised this problem and has suggested as a solution to attach the sensitizers to certain non-cross-linked polymers. Because the polymeric photosensitizers thus obtained have solubility characteristics which differ from the produced vitamin D compounds or previtamin D compounds, the polymeric photosensitizers can be separated from the desired product after the photochemical conversion. According to the abovementioned European Patent Application this separation is carried out by using two different solvent systems, one in which both the previtamin D reaction product and the polymeric photosensitizer are soluble, and another one in which the previtamin D reaction product is soluble but the polymeric photosensitizer is non-soluble. In this manner the polymeric photosensitizer can be separated from the reaction mixture after the photochemical conversion.

In practice, such a photochemical conversion of tachysterol compounds into previtamin D compounds must be carried out on a large scale, in particular for the production of vitamin D$_2$ and vitamin D$_3$. This means that this process requires large quantities of solvents. The use of several solvents in such a large-scale production process is a serious disadvantage because the process requires extra operations using large quantities of solvents. As a matter of fact, the solvents must be separated from each other, for example, by distillation, to enable their re-use in a subsequent batch. In an even more unfavourable case the solvents used form an azeotropic mixture, as a result of which the desired separation becomes even more difficult, if not impossible.

It is the object of the present invention to provide a method for the photochemical conversion of tachysterol compounds into previtamin D compounds and of trans-vitamin D compounds into cis-vitamin D compounds under the influence of radiation, by exposing the tachysterol compound and trans-vitamin D compound, respectively, dissolved in a suitable solvent system, in the presence of a polymeric photosensitizer consisting of a polymer chain ("backbone") comprising covalently bound sensitizers suitable for the photochemical conversion, to light with a wavelength at which the sensitizer absorbs, preferably between approx. 300 and approx. 1,000 nm, and by then isolating the resulting previtamin D compound and cis-vitamin D compound, respectively, in a way in which the above disadvantage does not occur.

According to the invention this object can be achieved by using in the photochemical conversion a polymeric photosensitizer, the polymer chain of which has been selected from the group consisting of a polyether chain, an amino groups-containing polymer chain and a block copolymer chain comprising polyether segments and/or amino groups-containing polymer segments, in such a manner that the polymeric photosensitizer dissolves in the solvent system during the exposure to radiation but either upon cooling precipitates from the solution and can be separated, or, in case said polymer chain comprises amino groups, can be protonated with a suitable acid substance and be removed in an aftertreatment.

It has been found that a photosensitizer having one of the above-mentioned polymer chains shows such a favourable solubility behaviour that one single solvent system suffices to separate the photosensitizer easily from the solution after the photochemical conversion. The term solvent system is to be understood to mean herein one single organic solvent, for example, an ether like diethyl ether, tetrahydrofuran or methyl-t.butyl ether, a (cyclo)alkane like cyclohexane, an alcohol like ethanol or methanol, an ester like methyl acetate or ethyl acetate, and the like, but also a mixture of solvents which can be re-used for a subsequent batch without separation in the individual components, for example, a mixture of two or more of the solvents mentioned hereinbefore. The desired separation of the photosensitizer from the solution can then be realised very easily by cooling the solution after the exposure to radiation, in which the polymeric photosensitizer precipitates and can be separated by filtering or centrifuging. The polymeric photosensitizer separated and recovered in this manner may then be re-used in a subsequent batch. Alternatively, a polymeric photosensitizer comprising amino groups can be protonated with a suitable acid substance and be removed in an after-treatment. This alternative method of removing the polymeric photosensitizer from the vitamin D product is even preferred because of its simplicity and its efficiency. As a matter of fact, after the irradiation in a solvent that is not miscible with water the reaction product can easily be freed from the photosensitizer by a simple extraction with dilute acid. This will be explained in more detail hereinafter. The polymeric photosensitizer can easily be recovered from the aqueous phase by deprotonation with a suitable base, if desired.

Suitable polymeric photosensitizers which may be used for the conversion according to the invention are photosensitizers having a polyoxy($C_2$–$C_6$)alkylene chain. Photosensitizers having a polyoxyethylene chain or a polyoxytetramethylene chain are to be preferred because such polymeric photosensitizers are readily accessible preparatively. The solubility behaviour of the polymeric photosensitizer can be adapted by a suitable choice of the degree of polymerisation of the polyoxyalkylene chain. As a result of the good solubility of polyoxyethylene compounds in water, in principle also the last traces of photosensitizers with polyoxyethylene chains can be removed from the product by a simple after-treatment with water.

In order to achieve an optimum choice in the process conditions it is advantageous when the solubility characteristics of the polymeric photosensitizer can be adapted to the most suitable solvent system. This is possible by using a photosensitizer having a block copolymer chain, the polyether segments and/or amino groups-containing segments being alternated by other polymer segments selected at will. By a correct choice of these "other" polymer segments, i.e. the choice of the chemical composition and of the length of the said polymer segments, the desired solubility characteristics and the crystallisability can even be further satisfied, resulting in "tailor-made" polymer chains. Examples of these "other" polymer segments are polymerisation products of various monomers, for example, styrene, styrene derivatives, methacrylic acid esters or amides, and other suitable unsaturated substances. Suitable polymeric photosensitizers are photosensitizers having a block copolymer chain which comprises polyoxy($C_2$–$C_6$)alkylene segments, preferably polyoxyethylene segments or polyoxytetramethylene segments, alternated by the "other" polymer segments mentioned hereinbefore.

Polymeric photosensitizers which may be used for the conversion according to the invention may also comprise amino groups-containing polymer chains, e.g. polyamine chains. These photosensitizers are preferred, because such photosensitizers have the great advantage that they can be extracted with dilute acids. As a matter of fact, the amino groups are protonated in acidic media, after which the formed polyammonium compounds easily dissolve in water. In this manner even the last traces of photosensitizer can easily be removed from the product, dissolved in a solvent that is not miscible with water, by a simple after-treatment with dilute acid. For such an after-treatment poly-acids, for example, polyacrylic acid or polystyrenesulphonic acid, may also be used successfully, the formed polymeric electrolytic complexes precipitating and being removed easily by filtration; this last method is suitable, in particular for an irradiation reaction performed in a water miscible solvent system. Polymeric photosensitizers having a polyamine chain may be built up from secondary or tertiary amines. In connection with the availability and solubility characteristics, including the crystallisability, a photosensitizer is preferred the polymer chain of which has been selected from the group consisting of a polyiminoethylene chain and a poly-N-($C_1$–$C_8$)alkyliminoethylene chain. As will become apparent from the examples a polymeric photosensitizer having a poly-N-tert.butyliminoethylene chain has proved to be excellently suitable.

Polyamines may also be used equally advantageously in block copolymers as chains for the polymeric photosensitizers which may be used for the conversion according to the invention. In addition to such polyamine segments, polyether segments may also be incorporated in the said block copolymer chains. Polyamine segments suitable for the said block copolymer chains are segments selected from polyiminoethylene and poly-N-($C_1$–$C_8$)alkyliminoethylene. A polymeric photosensitizer having a block copolymer chain which comprises poly-N-tert.butyliminoethylene segments is excellently suitable.

Other suitable amino groups-containing polymer chains are derived from amino groups-containing polymers, e.g. amino groups-containing polymethacrylate, which can be obtained by polymerising monomers having an amino group or having a functional group capable of introducing an amino group.

Sensitizers which are suitable for the photochemical conversion and which are covalently bound to the polymer chain are described in European Patent Application 252740 mentioned hereinbefore. Such sensitizers are also suitable for effectively catalysing the photochemical conversion according to the invention while bound to the polymeric chain defined hereinbefore. Polymeric photosensitizers to be used for the photochemical conversion according to the invention preferably comprise sensitizers derived from anthracene, an anthracene compound or a substituted thiophene compound. Examples of anthracene compounds are halogenated anthracenes like chlorinated and brominated anthracenes, alkylated anthracenes like methylated anthracenes, nitrated anthracenes and anthracenes having carbonyl substituents, carboxy groups, haloalkyl groups, sulphonyl groups, amino groups, alkoxy groups, aminocarbonyl groups, and the like. Examples of substituted thiophene compounds are substituted thiophene, bithienyls and terthienyls, in which the substituents may be selected from the substituents mentioned for the anthracene compounds and from aromatic substituents, for example, whether or not substituted phenyl, pyridyl, thienyl, and the like. In order to be able to synthesise the desired polymeric photosensitizer, the sensitizer molecule must have a suitable reactive group. Examples of reactive groups suitable for anthracene and anthracene compounds as well as for substituted thiophene compounds are carboxy, halomethyl amino, lower aminoalkyl, chlorosulphonyl, and the like.

The present invention also relates to polymeric photosensitizers to be used for the photochemical conversion described hereinbefore. A photosensitizer according to the invention comprises a polymer chain selected from the group consisting of a polyoxy($C_2$–$C_6$)alkylene chain, an amino groups-containing polymer chain, and a block copolymer chain comprising segments selected from the group consisting of polyoxy($C_2$–$C_6$)alkylene and amino groups-containing polymers. The polymeric photosensitizer according to the invention preferably comprises a polymer chain selected from a polyoxyethylene chain, a polyoxytetramethylene chain, a poly-N-tert.butyliminoethylene chain, an amino groups-containing polymethacrylate chain, and a block copolymer chain comprising polyoxyethylene segments and/or polyoxytetramethylene segments. Sensitizers suitable for such polymeric photosensitizers are derived from anthracene, an anthracene compound or a substituted thiophene compound.

An example of an excellently suitable polymeric photosensitizer according to the invention is a polymeric compound which consists of poly-N-tert.butyliminoethylene, provided with two anthryl groups or terthienyl groups, the polymer chain of which may optionally be interrupted by other polymer segments, for example, polyether segments like polytetrahydrofuran(THF)-segments. As will become apparent from the examples, such a polymeric photosensitizer may be prepared by polymerising tert.butylaziridine optionally in the presence of other polymer segments as indicated hereinbefore. The polymerisation of N-tert.butylaziridine may be initiated with a suitable initiator system which comprises e.g. anthryl groups or terthienyl groups. As an initiator system may be used, for example, a combination of a halomethylanthracene and a silver salt of a non-nucleophilic acid. After the polymerisation the active centres may be terminated with other compounds suitable for this purpose, for example, with an anthracene compound like an anthracene carboxylic acid or with a terthienyl compound. The resulting poly-N-tert.butyl-iminoethylene terminally provided with two anthryl groups or terthienyl groups and optionally interrupted by other polymer segments, e.g. polyTHF segments, may then be purified, for example, by pouring the polymer solution in a liquid medium in which the formed polymeric photosensitizer is insoluble, or by crystallisation from a suitable solvent. According to a likewise suitable method the polymeric photosensitizer may be prepared by carrying out the polymerisation in the absence of sensitizer and then terminating the formed polymer chain, comprising an active centre or active centres, respectively, at one end or at each end thereof, by a reaction with a suitable anthracene compound or terthienyl compound. This method is also illustrated in the examples.

Figure 1B:
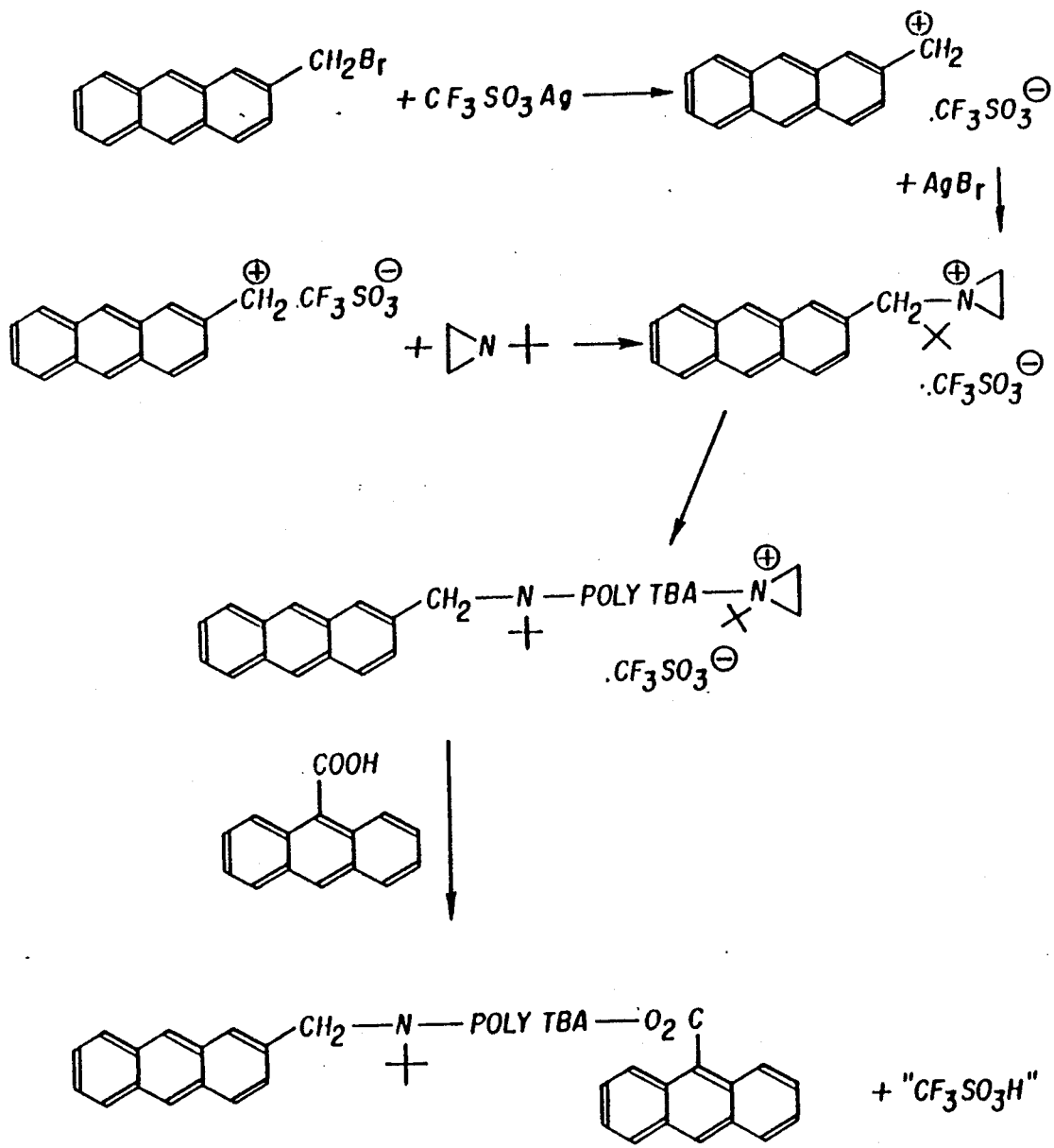

FIG. 1 shows the reaction scheme of Example I.
FIG. 2 shows the reaction scheme of Example II.

The invention will now be described in greater detail with reference to the ensuing specific examples.

EXAMPLE I

Synthesis of an $\alpha,\omega$-dianthryl terminated polyTBA-polyTHF block copolymer.

The reaction equations of the synthesis to be described hereinafter are recorded in the attached reaction scheme A.

Tetrahydrofuran (THF) is dried by refluxing on sodium metal until a deep blue colour remains when adding benzophenone. 100 ml of the so-dried THF are distilled directly into a dry 250 ml double-necked flask comprising a magnetic stirring rod. The second neck comprises a glass cock which remains opened during the distillation and which is sealed from atmospheric moisture by means of a calcium chloride tube. After the distillation, the $CaCl_2$ tube is replaced by a rubber or PVC tube for dry nitrogen. Under a light nitrogen flow the flask is removed from the distillation unit and placed in a thermostat bath of 20° C. and which comprises a magnetic stirring plate at the bottom. After stirring for 10 minutes to bring the temperature of the THF at 20° C., 286 mg (170 ul) of trifluoromethanesulphonic anhydride are injected into the THF by means of a pipette or injection needle, under a nitrogen flow and while stirring vehemently. After two minutes, still under nitrogen, 8 g of dry and freshly distilled N-tert.butylaziridine (TBA) are added to the solution which is constantly stirred. Ten minutes later 1 g of anthracenene-9-methylamine is added to the solution. After 30 minutes the solution is transferred to a dropping funnel and added slowly (10 minutes) to 1 liter of methanol which is cooled in an ice bath and which is stirred rapidly by means of a magnetic stirrer. After all has been added, the mixture is kept at 0° C. without stirring for 1 hour. The precipitate is filtered off on a glass filter. 8.5 g of an ABA block copolymer polyTBA-polyTHF-polyTBA with segment masses 4000-800-4000 (calculated) comprising two anthryl terminal groups are obtained.

The resulting block copolymer is identified by means of NMR and GPC (gel permeation chromatography). All relevant groups, including the anthryl terminal groups, can be observed in the NMR spectrum. The found molecular weight is in agreement with the calculated weight: approximately 9,000. The solubility properties of the resulting block copolymer are determined in THF and in a mixture of THF and ethanol. The block copolymer easily dissolves at 50° C. (>10% w/v); it crystallises again upon cooling down to 0° C.

EXAMPLE II

Synthesis of an $\alpha,\omega$-dianthryl terminated polyTBA.

The reaction equations of the synthesis to be described hereinafter are recorded in the attached reaction scheme B.

The following reactions are carried out in the apparatus described in Example I. A solution of 2 mmol 2-bromomethylanthracene and 2 mmol of silver triflate (silver trifluoromethanesulphonate) in methylene chloride is stirred at 20° C. for 30 minutes. After sedimentation of the formed silver bromide the clear solution is transferred under a nitrogen flow to a reaction flask, after which 100 mmol N-tert.butylaziridine (TBA) are added, all this under dry and oxygen-free conditions. After polymerising at 20° C. for 10 minutes as described in Example I, the terminal reactive centres are terminated with 2,5 mmol of anthracene-9-carboxylic acid dissolved in methylene chloride. After working up the reaction mixture as described in Example I, approximately 9 g of polyTBA having two anthryl terminal groups are obtained. Identification is carried out again by means of NMR and GPC. The resulting polymer has a molecular weight of approximately 5,000.

EXAMPLE III

Synthesis of $\alpha,\omega$-dianthryl terminated polyethylene oxide (PEO).

A commercial polyethylene glycol having a molecular weight of at least 4,000 is used as starting material. This is converted into the corresponding ditosylate in the manner described by R. de Vos and E. Goethals, Makromol. Chem., Rapid Commun. 6, 53 (1985). The conversion into the dianthryl derivative is carried out as follows: A solution of 5.5 g of 9-aminomethyl-anthracene in 20 ml of acetonitrile is added to a solution of 10 g of PEO-ditosylate in 30 ml of dry acetonitrile. The mixture is refluxed for 2 hours under a mild nitrogen flow. The solvent is removed in vacuo (15 mm Hg) and the residue is dissolved in 40 ml of dry ethanol by heating at 40° C. after which the solution is cooled down to −15° C. After 5 hours the precipitate is filtered off on a glass filter having a cooling jacket (−15° C.), washed with cold ethanol and dissolved again in 40 ml of dry ethanol at 40° C. The solution is cooled again to −15° C. and after 5 hours the precipitate is filtered off in the same manner, washed with cold ethanol, and dried in vacuo at room temperature; 9.5 g of $\alpha,\omega$-dianthryl terminated PEO are obtained.

The NMR spectrum indicates that all relevant groups, including the anthryl terminal groups, are present in the resulting polymer.

From the above crystallisation experiments it clearly appears that the resulting polymeric sensitizer dissolves at high temperature, viz. 40° C., in the solvent used, namely ethanol, but precipitates from this solvent upon cooling to −15° C. The polymeric sensitizer easily dissolves even at 35° C. (20% w/v) and can be recovered therefrom upon cooling down to 20° C.

EXAMPLE IV

Photochemical isomerisation of tachysterol to previtamin D.

A polyTHF-polyTBA block-copolymeric photosensitizer is synthesized as described in example I. The total molecular weight of the polymeric photosensitizer is 4000, as measured by GPC (gel permeation chromatography) based on polystyrene standards. The ratio THF/TBA is approx. 27/73. According to UV-analysis the polymeric photosensitizer contains approx. 80 milligrams of anthracene per gram polymer.

In a typical irradiation experiment 250 milligrams of the polymeric photosensitizer are dissolved in methyl tert.butyl ether (MTBE). To this mixture is added a solution of approx. 200 mg tachysterol in hexane. Tachysterol is freshly prepared from its 3,5-dinitrobenzoate ester by saponification under nitrogen. Then the total volume is made up to 100 ml by MTBE. Irradiation is performed in a nitrogen atmosphere at 4° C. in a merry-go-round apparatus. The light-source is a high-pressure mercury lamp (Philips HPK-125). The wavelengths below 300 mm are filtered off by means of a filter solution consisting of NaBr, $Ag_2SO_4$ and $HgSO_4$ in water. The photochemical reaction is monitored by means of HPLC-analysis: see Table A.

TABLE A

| irradiation time (min) | % (w/w) previtamin D | % (w/w) tachysterol |
| --- | --- | --- |
| 0 | — | 0.219 |
| 5 | 0.056 | 0.162 |
| 10 | 0.110 | 0.103 |
| 20 | 0.202 | 0.013 |
| 40 | 0.201 | 0.004 |

The polymeric photosensitizer is removed from the irradiation mixture by simply washing with 0,1N hydrochloric acid. After said washing the organic phase is free from photosensitizer.

EXAMPLE V

Synthesis of anthracene containing polyethylenimine.

Commercially available polyethylenimine (PEI), 50% solution in water, is dried by azeotropic distillation in the ternary system ethanol/toluene/water. After the drying procedure 4.8 g of the obtained PEI is dissolved in 50 g of dry ethanol, and 0.485 g of 9-chloromethylanthracene are added. The mixture is refluxed for nine hours. After standing for three days at room temperature the unreacted starting material has precipitated and is filtered off. The polymeric product is stored as a solution in ethanol. One gram of dry polymeric photosensitizer contains about 70 mg of anthracene according to UV-analysis. The polymeric photosensitizer is well soluble in dilute hydrochloric acid and can therefore simply be removed from the final product, dissolved in a non-water-miscible solvent like methyl tert.butyl ether, by washing with dilute acid.

EXAMPLE VI

Synthesis of a polyTHF-polyTBA block-copolymer containing terthienyl.

To 70 ml of dry THF (dried over calciumhydride and distilled from sodium wire before use) is added 144 μl of trifluoromethanesulfonic anhydride at room temperature. After two minutes 1.81 g TBA is added and the temperature is kept at room temperature. Ten minutes later 3.0 mmol of 5-aminomethyl-2,2′:5′,2″-terthienyl are added. After 10 minutes the temperature of the reaction mixture is raised to 35° C. After reacting for 15 minutes the reaction mixture is poured onto 700 ml of cold methanol. The precipitate is filtered off and dried, and is identified as a polyTHF-polyTBA block-copolymer containing terthienyl end groups. The behaviour towards dilute acids is equal to that of the product described in Example V.

EXAMPLE VII

Synthesis of polyoxyethylene containing anthracene via a spacer attached to the polymer chain.

Polyoxyethylene glycol (average molecular weight 4000; PEG-4000) is dried under vacuum at 60° C. for three hours. 1,6 g of the so-dried PEG-4000 is dissolved in 25 ml benzene at 60° C., after which 3.4 g of hexamethylenediisocyanate is added. The reaction is carried out for two days at 60° C. in a nitrogen atmosphere. The intermediate, i.e. the reaction product of HMDI with PEG-4000, is separated by precipitation from dry ethyl ether. After filtration the intermediate is again dissolved in dry benzene and poured into cold diethyl ether. The precipitate is filtered off and washed 5 times with 50 ml of dry diethyl ether. The purification of the intermediate is carried out under nitrogen.

The obtained reaction product of HMDI and PEG-4000 is then dissolved in 50 ml of dry benzene and 0.48 g of 9-aminomethylanthracene is added. The viscosity of the solution increases immediately. The reaction is carried out for 30 minutes at room temperature. After dilution with 25 ml of benzene the mixture is poured into dry diethyl ether. The precipitate is filtered off, dissolved again in dry benzene, poured into dry diethyl ether and, after filtration, washed 5 times with 50 ml of dry diethyl ether. The polymeric product is dried under vacuum for one hour. According to UV-analysis the polymeric photosenitizer obtained contains about 80 mg of anthracene per gram polymer. An irradiation experiment as in example 4 (using ethanol as solvent instead of MTBE) gives the following results as determined by HPLC: Table B

TABLE B

| irradiation time (min) | % (w/w) previtamin D | % (w/w) tachysterol |
| --- | --- | --- |
| 0 | — | 0.210 |
| 5 | 0.118 | 0.072 |
| 10 | 0.174 | 0.015 |
| 20 | 0.175 | 0.011 |

The solubility characteristics of the polymeric photosensitizer obtained are comparable with those of the product described in Example III.

EXAMPLE VIII

Synthesis of poly(N,N-dimethylaminoethyl methacrylate-copolymer-9 anthrylmethyl methacrylate).

9.5 g of N,N-dimethylaminoethyl methacrylate (purified by distillation under 1 mm Hg pressure, b.p. 40° C.), 0,5 g of 9-anthrylmethyl methacrylate, 0.1 g of 2,2'-azobis(butyronitrile) (recrystallized from methanol) and 10 ml of dry toluene are combined in a flask equipped with a bulb condenser. The flask is cooled to 0° C., evacuated using a water aspirator and then charged with a light positive pressure of argon. This procedure is repeated 5 times (6 times total) leaving a positive pressure of argon over the degassed solution.

The contents of the flask are stirred for 40 h at 60° C. After cooling to room temperature, the solution is diluted with 20 ml of toluene and added dropwise to 0.5 l vigorously stirred hexane cooled to −20° C. Precipitated copolymer is filtered off, dissolved in 30 ml of toluene and again added to 0.5 l vigorously stirred hexane cooled to −20° C. and filtered off. This procedure is repeated 2 times. After filtration the remaining solvent is removed by drying in vacuum leaving 7.2 g of glassy copolymer. If the copolymer is dissolved in benzene and dried by lyophilisation it is a powder that can be more easily handled than when obtained by evapoation of the solvent under vacuum. The average molecular weight ($M_n$) of the copolymer, determined by Vapour Pressure Osmometry, is 18500. UV analysis of the title copolymer shows that the copolymer contains approx. 30 mg of anthracene per gram of copolymer. The partition coefficient of the copolymer between 0.1N HCl and MTBE (methyl tert.butyl ether) is approx. 25, according to UV-analysis. Consequently the polymeric photosensitizer can easily be removed by a simple washing with dilute acid.

We claim:

1. A method for the photochemical conversion of tachysterol compounds into previtamin D compounds and of trans-vitamin D compounds into cis-vitamin D compounds under the influence of radiation by exposing the tachysterol compound and trans-vitamin D compound, respectively, dissolved in a solvent system, in the presence of a polymeric photosensitizer consisting of a polymer chain comprising covalently bound sensitizers for the photochemical conversion, to light with a wavelength of between approximately 300 and approximately 1,000 nm, and by then isolating the resulting previtamin D compound and cis-vitamin D compound, respectively, characterised in that a polymeric photosensitizer is used, the polymer chain of which has been selected from the group consisting of a polyether chain, an amino groups-containing polymer chain and a block copolymer chain comprising polyether segments and/or amino groups-containing polymer segments, in such a manner that the polymeric photosensitizer dissolves in the solvent system during exposure to radiation but either upon cooling precipitates from the solution and can be separated, or, in case said polymer chain comprises amino groups, can be protonated with an acid substance and be removed in an after-treatment.

2. A method as claimed in claim 1, characterised in that a polymeric photosensitizer is used having a polyoxy($C_2$–$C_6$)-alkylene chain.

3. A method as claimed in claim 2 characterized in that the polyoxy ($C_2$–$C_6$)-alkylene chain is selected from a polyoxyethylene chain or a polyoxytetramethylene chain.

4. A method as claimed in claim 1, characterised in that a polymeric photosensitizer is used having a block copolymer chain which comprises polyoxy($C_2$–$C_6$)alkylene segments.

5. A method as claimed in claim 4 characterized in that the polyoxy ($C_2$–$C_6$) alkylene segments are selected from polyoxyethylene segments or polyoxytetramethylene segments.

6. A method as claimed in claim 1, characterised in that a polymeric photosensitizer is used the polymer chain of which has been selected from a polyiminoethylene chain, a poly-N-($C_1$–$C_8$)alkyliminoethylene chain, and an amino groups-comprising polymethacrylate chain.

7. A method as claimed in claim 6, characterised in that a polymeric photosensitizer is used having a poly-N-tert.butyliminoethylene chain.

8. A method as claimed in claim 1, characterised in that a polymeric photosensitizer is used having a block copolymer chain comprising segments selected from polyiminoethylenes poly-N-($C_1$–$C_8$)alkyliminoethylene and amino groups-comprising polymethacrylate.

9. A method as claimed in any of the preceding claims, characterised in that a polymeric photosensitizer is used the sensitizers of which are derived from anthracene, an anthracene compound or a substituted thiophene compound.

* * * * *